United States Patent [19]

Goof

[11] Patent Number: 4,696,644

[45] Date of Patent: Sep. 29, 1987

[54] TOOTH CLEANING INSTRUMENT

[76] Inventor: Sven K. L. Goof, 236A, Gl. Strandvej, DK-3050 Humlebaek, Denmark

[21] Appl. No.: 758,672.

[22] PCT Filed: Nov. 12, 1984

[86] PCT No.: PCT/DK84/00106

§ 371 Date: Jul. 10, 1985

§ 102(e) Date: Jul. 10, 1985

[87] PCT Pub. No.: WO85/02107

PCT Pub. Date: May 23, 1985

[30] Foreign Application Priority Data

Nov. 11, 1983 [DK] Denmark ............................ 5176/83

[51] Int. Cl.$^4$ ................................................ A61C 3/02
[52] U.S. Cl. ........................................ 433/88; 433/125
[58] Field of Search ........................... 433/84, 88, 125; 51/438, 436, 426, 227, 228, 321, 439

[56] References Cited

U.S. PATENT DOCUMENTS

| | | | |
|---|---|---|---|
| 2,324,250 | 7/1943 | Voerge | 51/439 |
| 2,669,809 | 2/1954 | McGrath | 51/439 |
| 4,462,803 | 7/1984 | Landgraf et al. | 433/88 |
| 4,482,322 | 11/1984 | Hain et al. | 433/88 |

Primary Examiner—Robert Peshock
Attorney, Agent, or Firm—Tilton, Fallon, Lungmus

[57] ABSTRACT

An instrument for cleaning teeth by blowing a powdered abrasive thereon includes a distal nozzle end (10) at which a central conduit (12) has an outlet portion (16) for supplying abrasive and drive gas therefor, and a surrounding annular passage (14) supplying water under pressure. The outlet portion (16) of the central conduit (12) continues beyond an outlet (18) of the annular passage, the outlet (18) being shaped as a restricted annular slot or throttle throat. Thus, a vacuum is created at the outlet portion (16) of the central conduit and this vacuum stabilizes the water jets and thereby counteracts splashes during the use of the instrument.

4 Claims, 1 Drawing Figure

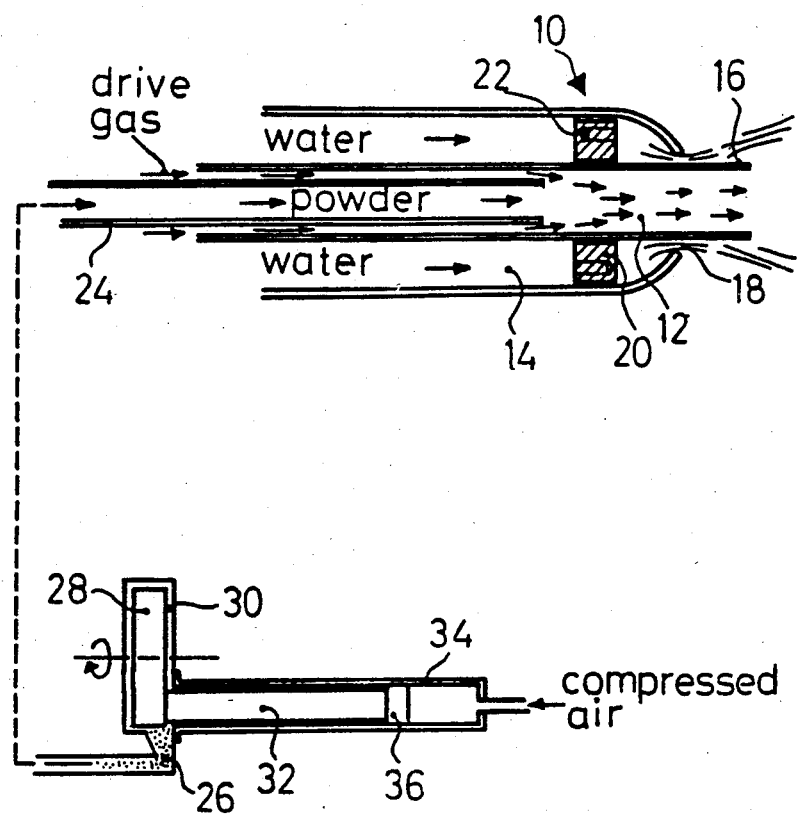

TOOTH CLEANING INSTRUMENT

The present invention relates to an instrument for cleaning especally teeth by blowing a powdered abrasive thereon and wherein, besides, the instrument is of the type stated in the opening clause of claim 1.

Instruments of this type are known from U.S. Pat. Nos. 3,882,638 and 4,174,571. In practice, however, these known instruments have proved to give a very strong and inconvenient splashing. Furthermore, it is recommended, or even prescribed, that the operator of the instrument should carry a face mask and gloves for protection against splashes. This is due to the fact that certain abrasives are rather strongly alkaline in aqueous solution. Also, there have been cases where the patients have had their contact lenses spoilt because of splashes of alkaline abrasive solutions.

The strong splashing from the known instruments is a considerable disadvantage which is overcome by the instrument according to the invention which is characterized by the features stated in the characterizing clause of claim 1. Thus, the restricted annular slot or throat has the effect that a vaccum is created which stabilizes the water discharged and only very little splashing occurs. This stabilizing effect is further enhanced by the embodiment according to claim 2.

The invention will now be described in further detail with references to the drawing which is a schematic presentation of an embodiment of the instrument of the invention.

An instrument according to the invention comprises a handpiece (not shown) having a distal nozzle portion 10 at which a centrally positioned conduit 12 has an outlet and supplies powdered abrasive mixed with drive gas. Around the central conduit 12 there is defined an annular passage 14 which supplies water under pressure. The outer or foremost portion 16 of the central conduit 12 continues beyond an outlet portion of the annular passage which is shaped as a restricted annular slot or throat 18. Hereby, a vacuum is created immediately at and around the outlet of the central conduit 12, and this vacuum stabilizes both the outflow of water and the outflow of air and abrasive powder. The embodiment shown further includes a rotor ring 20 which is located in the annular passage 14 upstream of the restricted outlet 18 thereof. The ring 20 is supported freely rotatable on or around the wall of the central conduit 12. The rotor ring 20 substantially fills out the flow sectional area of the annular passage 14 and, therefore, the water is forced through inclined nozzle passages 22 extending through the ring 20 in such a manner that the jets of water rotate the ring. Instead of the drilled passages 22 shown, inclined grooves extending in the periphery of the rotor ring may also be provided.

In the embodiment shown the supply of abrasive powder takes place through a tube 24 inserted coaxially in the central conduit 12. Drive gas for the abrasive powder is supplied through an annular passage defined between the outside of the tube 24 and the inside of the central conduit 12. The discharge portion of the powder supply tube 24 is retracted relative to the outlet portion 16 of the central conduit 12 and, thereby, the drive gas thus supplied produces a suction effect sufficient to draw the abrasive powder through the supply tube 24 and to drive the powder further forward and out of the outlet portion 16 of the central conduit 12.

In the embodiment shown the inlet end of the powder supply tube 24 is connected with a chamber 26 containing or receiving abrasive powder. In a specific embodiment, the chamber 26 collects abrasive powder produced by a grinding disc 28 rotating in a closed housing 30. In the side of the housing an opening is provided in which a cylindrical bar 32 of abrasive may be inserted and retained relative to the grinding disc. The bar 32 may preferably be inserted in a cylindrical guide cylinder 34 comprising a slidable piston 36. When pressurized gas is supplied, the piston 36 is capable of continuously keeping the bar 32 in contact with the grinding disc 28 at a constant pressure of contact.

Embodiments as that shown in the drawing are particularly suited for use with water soluble abrasives, partly because no significant splashing occurs during the use of the instrument, and partly because of the construction of the supply system for the powder. Thus, powder of water-soluble abrasives strongly tends to lump and form coatings internally in passages, if the powder has the possibility to absorb humidity.

In known instruments for use with water soluble abrasives it has thus been necessary to constantly keep the powder in motion in a store container by means of pressurized gas. Such provisions are not required in the instrument of the invention wherein the powder is not produced until immediately before use. Besides, the entire powder tube system may be blown empty for powder just by closing the outlet 16 of the central conduit 12 while drive gas is still being supplied.

I claim:

1. An instrument for discharging powdered abrasive and water for cleaning surfaces, especially tooth surfaces, said instrument comprising
   a handpiece having a distal nozzle portion (10) defining an end opening,
   a central conduit (12) for conducting abrasive material and gas, said central conduit extending longitudinally through said nozzle portion and having an outlet portion (16) protruding through, and extending a substantial distance beyond, said end opening, and
   an annular water passage (14) defined in said nozzle portion about said central conduit for supplyiing water to said end opening, said nozzle portion having converging inside wall surfaces defining, in combination with the outer surface of said central conduit, a constricted, annular throttle throat (18) at said end opening for discharging water about and against said outlet portion (16) protruding through and beyond said end opening.

2. An instrument for discharging powdered abrasive and water for cleaning surfaces, especially tooth surfaces, said instrument comprising
   a handpiece having a distal nozzle portion (10) defining an end opening,
   a central conduit (12) for conducting abrasive material and gas, said central conduit extending longitudinally through said nozzle portion and having a outlet portion (16) protruding through, and extending a substantial distance beyond, said end opening,
   an annular water passage (14) defined in said nozzle portion about said central conduit for supplying water to said end opening, said nozzle portion and central conduit being shaped and dimensioned to define a constricted, annular throttle throat (18) at said end opening for discharging water about and against said outlet portion (16) protruding through and beyond said opening, and a rotor ring (20) rotatably mounted upon said central conduit (12) within said annular water passage (14) and upstream of said annular throttle throat (18), said rotor ring (20) occupying substantially the entire cross sectional area of said annular passage (14) and being provided with a circumferential series of nozzle passages (22) extending therethrough, said nozzle passages (22) being inclined in relation to the axis of said rotor ring so that water under pressure flowing through said nozzle passages rotates said ring.

3. The instrument of claim 2, wherein said central conduit (12) includes an abrasive supply tube (24) concentrically disposed therein, said abrasive supply tube being smaller than the interior of said central conduit (12) to define an annular passage therebetween for the flow of drive gas, and said abrasive supply tube having a discharge end terminating a substantial distance upstream from the outlet portion (16) of said central conduit (12).

4. An instrument for discharging powdered abrasive and water for cleaning surfaces, especially tooth surfaces, said instrument comprising a handpiece having a distal nozzle portion (10) defining an end opening, a central conduit (12) for conducting abrasive material and gas, said central conduit extending longitudinally through said nozzle portion and having an outlet portion (16) protruding through, and extending a substantial distance beyond, said end opening, an annular water passage (14) defined in said nozzle portion about said central conduit for supplying water to said end opening, said nozzle portion and central conduit being shaped and dimensioned to define a constricted, annular throttle throat (18) at said end opening for discharging water about and against said outlet portion (16) protruding through and beyond said opening, said central conduit (12) including an abrasive supply tube (24) concentrically disposed therein, said abrasive supply tube being smaller than the interior of said central conduit (12) to define an annular passage therebetween for the flow of drive gas, and said abrasive supply tube having a discharge end terminating a substantial distance upstream from the outlet portion (16) of said central conduit (12).

* * * * *